(12) United States Patent
Diaz-Chiosa et al.

(10) Patent No.: US 11,766,510 B2
(45) Date of Patent: Sep. 26, 2023

(54) WEARABLE MICRODIALYSIS DEVICE FOR EARLY DETECTION OF ANASTOMOTIC LEAKS

(71) Applicant: Covidien LP, Mansfield, MA (US)

(72) Inventors: Olesea Diaz-Chiosa, Naugatuck, CT (US); Stanislaw Z. Marczyk, Stratford, CT (US)

(73) Assignee: Covidien LP, Mansfield, MA (US)

( * ) Notice: Subject to any disclaimer, the term of this patent is extended or adjusted under 35 U.S.C. 154(b) by 289 days.

(21) Appl. No.: 16/871,288

(22) Filed: May 11, 2020

(65) Prior Publication Data

US 2021/0346583 A1    Nov. 11, 2021

(51) Int. Cl.
  *A61M 1/28* (2006.01)
  *A61M 1/16* (2006.01)

(52) U.S. Cl.
  CPC .......... *A61M 1/285* (2013.01); *A61M 1/1627* (2014.02); *A61M 2205/04* (2013.01);
  (Continued)

(58) Field of Classification Search
  CPC ............... A61M 1/285; A61M 1/1627; A61M 2205/04; A61M 2205/15; A61M 2205/3303; A61M 2205/502; A61M 2209/088; A61M 2230/201; A61M 2025/0042; A61M 5/14244; A61B 5/4255; A61B 5/14528; A61B 5/02438; A61B 5/4836; A61B 5/686; G16H 40/67; G16H 40/63; G16H 10/60; G16H 10/65; G16H 20/13; G16H 20/17; G16H 20/10
  See application file for complete search history.

(56) References Cited

U.S. PATENT DOCUMENTS

2010/0179397 A1*  7/2010  Bright ............... A61B 5/00
                                                    600/309
2014/0165255 A1*  6/2014  Hanberger ........ A41D 13/1281
                                                    2/69
(Continued)

FOREIGN PATENT DOCUMENTS

CN          103932718 A  *  7/2014  ........... A61B 5/1427
WO  WO-2006119914 A2  *  11/2006  ......... A61B 5/14528
WO         2016189301 A1     12/2016

OTHER PUBLICATIONS

Matthiessen, Peter, et al. "Is Early Detection of Anastomotic Leakage Possible y Intraperitoneal Microdialysis and Intraperitoneal Cytokines After Anterior Resection of the Rectum for Cancer?" Diseases of the Colon & Rectum vol. 50, pp. 1918-1927 (printed 2007, presented Aug. 2005) (Year: 2005).*

(Continued)

*Primary Examiner* — Magali P Slawski
*Assistant Examiner* — Bernadette Karen McGann
(74) *Attorney, Agent, or Firm* — Carter, DeLuca & Farrell LLP (57) ABSTRACT

A system for detecting and treating an anastomotic leak includes a microcatheter implanted at an anastomosis site; a source of a perfusion fluid coupled to the microcatheter and configured to dispense the perfusion fluid to the microcatheter; and an analyzer coupled to the microcatheter configured to receive an extracellular fluid from the microcatheter and to analyze the extracellular fluid to determine status of the anastomosis site.

11 Claims, 4 Drawing Sheets

(52) U.S. Cl.
CPC . *A61M 2205/15* (2013.01); *A61M 2205/3303* (2013.01); *A61M 2205/502* (2013.01); *A61M 2209/088* (2013.01); *A61M 2230/201* (2013.01)

(56) References Cited

U.S. PATENT DOCUMENTS

| | | | |
|---|---|---|---|
| 2018/0136247 A1 | 5/2018 | Boutelle et al. | |
| 2019/0313968 A1* | 10/2019 | Castagna | A61B 5/0024 |
| 2022/0265175 A1* | 8/2022 | Helwa | A61B 5/1473 |

OTHER PUBLICATIONS

English machine translation of WO 2006/119914 (Year: 2006).*
Machine generated translation of CN 103932718 A (Year: 2014).*
Matthiessen, Peter et al., "Is Early Detection of Anastomotic Leakage Possible by Intraperitoneal Microdialysis and Intraperitoneal Cytokines After Anterior Resection of the Rectum for Cancer", Diseases of the Colon & Rectum, Lippincott Williams and Wilkins, vol. 50, No. 11, Sep. 1, 2007, pp. 1918-1927.
Pedersen, Mark, et al., "Mediastinal Microdialysis: Early Diagnosis of Anastomotic Leakage After Resection for Esophageal Cancer", Esophagus, Springer-Verlag, vol. 6, No. 1, Mar. 18, 2009, pp. 63-66.
Extended European Search Report dated Oct. 12, 2021 issued in corresponding EP Appln. No. 21173014.8.
Deeba et al. "Use of Rapid Sampling Microdialysis for Intraoperative Monitoring of Bowel Ischemia" Dis Colon Rectum. Sep. 2008. 51(9):1408-13. doi: 10.1007/s10350-008-9375-4. Epub May 24, 2008.
User Manual for CMA 600 Microdialysis Analyzer (Jun. 2010).

* cited by examiner

WEARABLE MICRODIALYSIS DEVICE FOR EARLY DETECTION OF ANASTOMOTIC LEAKS

BACKGROUND

Intestinal anastomosis may be performed using various techniques and medical devices, such as end-to-end stapling devices, which are used in colorectal surgery to connect portions of colon, large intestines, etc. Anastomosis may result in post-operative complications, such as anastomotic leaks. The root causes of the leaks are not completely known, but several factors increase the risk of leaks, such as certain medical conditions, including, diabetes, ischemia, infection, etc. There are two types of leaks: acute and chronic. Acute leaks occur within about 2 or 3 days post-operatively and are usually due to compromised integrity of anastomosis. Chronic leaks have a delayed onset from about 7 to about 30 days after the patient was discharged. Chronic leaks are a major post-operative complication and lead to peritonitis, sepsis, and morbidity. Patients who develop chronic leaks need endoscopic drainage, surgical intervention, and clinical monitoring. Monitoring is critical to determine the status of the leak. Depending on the extent of the leak, different management methods may be used, such as drainage, extensive laparotomy, as well as an open surgery, which has an elevated risk of permanent ostomy, especially for low rectal resection patients.

The current management of complications is reactive, treating a complication long after it occurred and advanced into systemic complication, such as sepsis. Such approaches have severe outcomes for both patient and hospital, ranging from reduced quality of life for the patient to increased resource use in treating the patient. Leak patients also have higher post-operative infection rates and spend on average 7 more days in the hospital, compared with non-leak patients. The extra days result in additional costs to the hospital. Thus, there is a need for a more proactive approach to anastomotic leak management through earlier diagnosis and intervention.

SUMMARY

The present disclosure provides a system and method for detecting early stages of leak formation following anastomosis as well as treating the detected anastomotic leak. Currently, there is a need for solutions for early anastomotic leak detection and diagnosis after stapling surgery. When the leaks occur, patients return to the hospital and require longer stay and are surgically managed. There are no minimally invasive, predictive solutions available to patients. The disclosed microdialysis approach would improve patient quality of life, as well as reduce the financial burden on the hospital, e.g., due to additional ICU, equipment and operating room costs.

The system includes a microcatheter, which is implanted at an anastomosis site using biodegradable sutures or other fixation means. The microcatheter is minimally invasive and mimics a blood capillary, providing for the exchange of fluids. Perfusion fluid, such as saline, is actively pumped by a portable pump into the anastomosis site. The concentration gradient drives exchange of saline and extracellular fluid from the anastomosis site. Extracellular fluid is collected via the microcatheter in a container or is passed directly to an analyzer, which is configured to detect specific molecules in the extracellular fluid. The analyte molecules may include early anastomotic leak biomarkers, which may be systemic parameters, such as C-reactive proteins, white blood cells, and metabolic parameters, pyruvate, lactate, and specific leak biomarkers, such as, interleukins, tumor necrosis factor α (TNF-α), and matrix metalloprotease. Concentration of these molecules are monitored over specific period, depending on the patient's risk of developing complications. The changes in biomarkers trends are suggestive of tissue healing progress. In embodiments, ratio of pyruvate to lactate is calculated, and is used to determine tissue oxygenation. Larger concentration of lactate is indicative of hypoxic or ischemic tissue, which correlates with tissue dehiscence, which in turn, results in anastomotic leaks. A consistent increase in lactate concentration is also a sign of an early leak.

According to one embodiment of the present disclosure, a system for detecting and treating an anastomotic leak is disclosed. The system includes a microcatheter implanted at an anastomosis site; a source of a perfusion fluid coupled to the microcatheter and configured to dispense the perfusion fluid to the microcatheter; and an analyzer coupled to the microcatheter configured to receive an extracellular fluid from the microcatheter and to analyze the extracellular fluid to determine status of the anastomosis site.

According to one aspect of the above embodiment, the microcatheter includes: an outer tube having a distal portion formed from a semipermeable membrane and defining a lumen within the outer tube; and an inner tube disposed within lumen. The outer tube is fluidly coupled to a return line and the inner tube is fluidly coupled to a supply line. The return line is coupled to the analyzer and the supply line is coupled to the source of the perfusion fluid.

According to another aspect of the above embodiment, the source of the perfusion fluid includes: a dispensing container including the perfusion fluid; and a pump fluidly coupled to the dispensing container and configured to meter the perfusion fluid at a configurable flow rate.

According to a further aspect of the above embodiment, the analyzer is configured to determine a presence of an anastomotic leak. The analyzer includes: a lactate sensor configured to measure a concentration of lactate; a pyruvate sensor configured to measure a concentration of pyruvate; and a processor configured to calculate a ratio of the concentration of lactate to the concentration of pyruvate. The processor is further configured to determine the presence of the anastomotic leak based on at least one of the concentration of lactate, the concentration of pyruvate, or the ratio of the concentration of lactate to the concentration of pyruvate. The analyzer further includes: a display coupled to the processor, the display configured to display a value selected from the group consisting of the concentration of lactate, the concentration of pyruvate, and the ratio of the concentration of lactate to the concentration of pyruvate. The display is configured to display a plot over time of the value.

According to another embodiment of the present disclosure, a system for detecting and treating an anastomotic leak is disclosed. The system includes: a microcatheter implanted at an anastomosis site; a source of a perfusion fluid coupled to the microcatheter and configured to dispense the perfusion fluid to the microcatheter; and an analyzer coupled to the microcatheter configured to receive an extracellular fluid from the microcatheter and to analyze the extracellular fluid to determine a presence of an anastomotic leak.

According to one aspect of the above embodiment, the microcatheter includes: an outer tube having a distal portion formed from a semipermeable membrane and defining a lumen within the outer tube, the outer tube is fluidly coupled to a return line, which is coupled to the analyzer; and an inner tube disposed within lumen, the inner tube is fluidly coupled to a supply line, which is coupled to the source of the perfusion fluid.

According to another aspect of the above embodiment, the source of the perfusion fluid includes: a dispensing container including the perfusion fluid; and a pump fluidly coupled to the dispensing container and configured to meter the perfusion fluid at a configurable flow rate.

According to a further aspect of the above embodiment, the analyzer includes: a lactate sensor configured to measure a concentration of lactate; a pyruvate sensor configured to measure a concentration of pyruvate; and a processor configured to calculate a ratio of the concentration of lactate to the concentration of pyruvate. The processor is further configured to determine the presence of the anastomotic leak based on at least one of the concentration of lactate, the concentration of pyruvate, or the ratio of the concentration of lactate to the concentration of pyruvate. The analyzer further includes a display coupled to the processor, the display configured to display a value selected from the group consisting of the concentration of lactate, the concentration of pyruvate, and the ratio of the concentration of lactate to the concentration of pyruvate.

According to a further embodiment of the present disclosure, a method for detecting and treating an anastomotic leak is disclosed. The method includes: implanting a microcatheter at an anastomosis site, the microcatheter coupled to a source of a perfusion fluid and an analyzer; supply the perfusion fluid to the microcatheter from the source of the perfusion fluid; collect an extracellular fluid at the microcatheter; and analyzing, at the analyzer, the extracellular fluid to determine a presence of an anastomotic leak.

According to one aspect of the above embodiment, the method further includes: measuring a concentration of lactate at the analyzer; measuring a concentration of pyruvate at the analyzer; and calculating, at the analyzer, a ratio of the concentration of lactate to the concentration of pyruvate.

The method further includes determining the presence of the anastomotic leak based on at least one of the concentration of lactate, the concentration of pyruvate, or the ratio of the concentration of lactate to the concentration of pyruvate. The method also includes displaying on the analyzer a value or a plot over time of the value, the value selected from the group consisting of the concentration of lactate, the concentration of pyruvate, and the ratio of the concentration of lactate to the concentration of pyruvate.

BRIEF DESCRIPTION OF THE DRAWINGS

Embodiments of the present disclosure are described herein with reference to the accompanying drawings, wherein.

DETAILED DESCRIPTION

Embodiments of the presently disclosed system are described in detail with reference to the drawings, in which like reference numerals designate identical or corresponding elements in each of the several views. As used herein the term "distal" refers to the portion of the surgical robotic system and/or the surgical instrument coupled thereto that is closer to the patient, while the term "proximal" refers to the portion that is farther from the patient.

The term "application" may include a computer program designed to perform functions, tasks, or activities for the benefit of a user. Application may refer to, for example, software running locally or remotely, as a standalone program or in a web browser, or other software which would be understood by one skilled in the art to be an application. An application may run on a controller, or on a user device, including, for example, a mobile device, an IOT device, or a server system.

Figure 1:
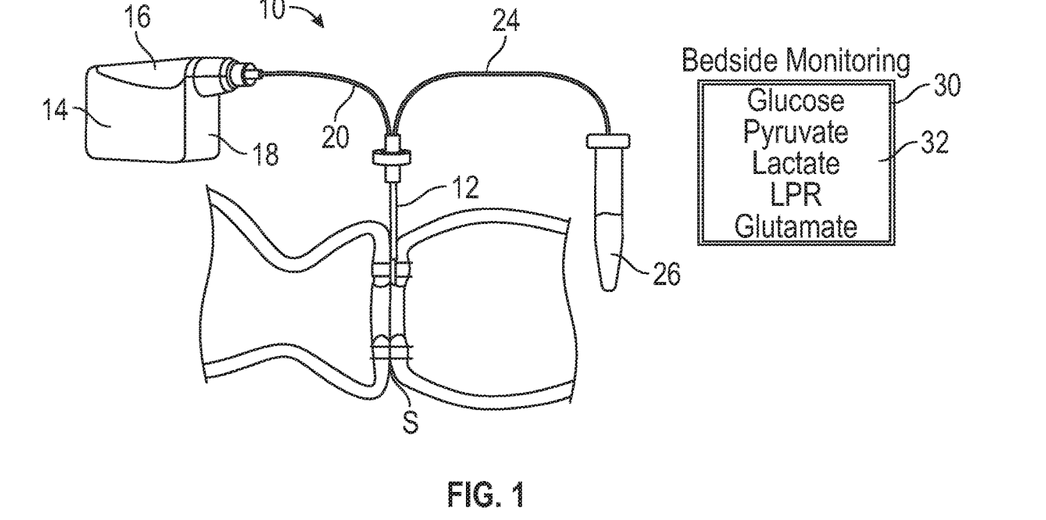
FIG. 1 is a schematic view of a system for detecting and treating an anastomotic leak with a microcatheter implanted at an anastomosis site according to an embodiment of the present disclosure.
Figure 2:
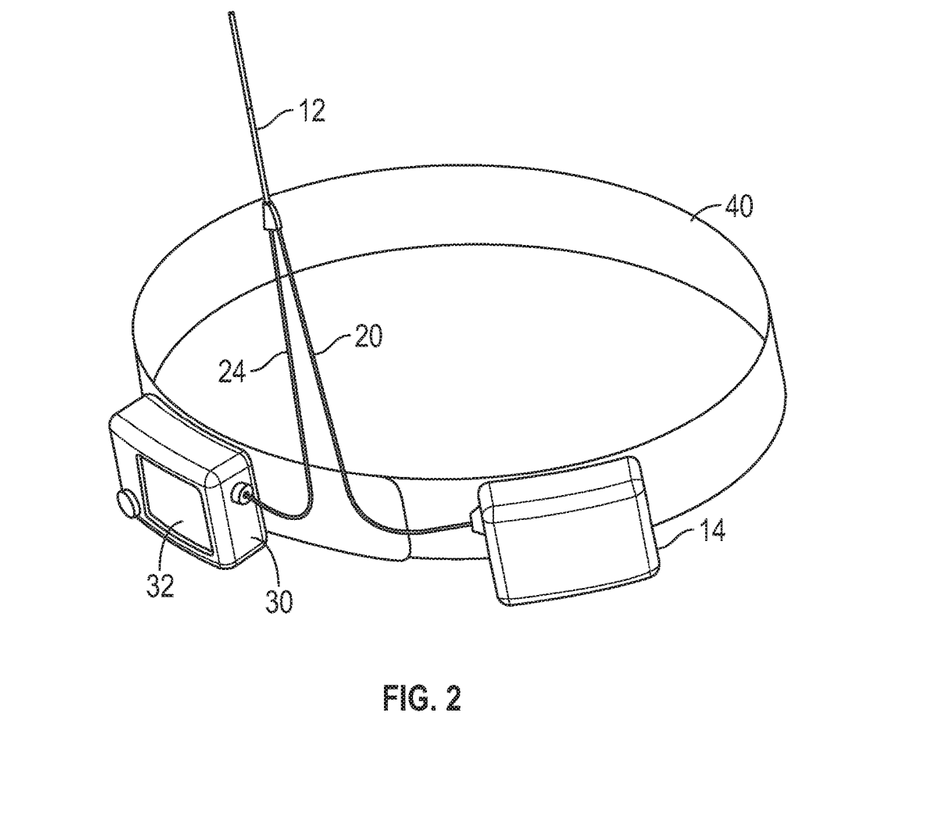
FIG. 2 is a perspective view of the system of FIG. 1 according to an embodiment of the present disclosure.

With reference to FIGS. 1 and 2, a system 10 for detecting and treating an anastomotic leak is shown. The system 10 includes a microcatheter 12 implanted at an anastomosis site "S". The anastomosis site can be created as part of any surgical procedure joining any two separated parts of an anatomical lumen, such as blood vessels, intestines, colon, and the like. Anastomosis may be performed using any surgical techniques using sutures, staplers, fasteners, adhesives, and any combinations thereof. The microcatheter 12 is used for micro detection at cellular level at the anastomosis site "S" or in the areas where another surgical intervention has greater risk of negative outcomes, such as in low rectal resection.

The microcatheter 12 may be secured at the anastomosis site "S" using sutures, staplers, fasteners, adhesives, which may be formed from a biodegradable material, such that after the material dissolves, the microcatheter 12 detaches, and can then be extracted from the anastomosis site "S". As used herein, the terms "biodegradable" and "bioabsorbable" are used with respect to a property of a material. "Biodegradable" is a material that is capable of being decomposed or broken down in vivo and subsequently excreted. "Bioabsorbable" is a material that is capable of being decomposed or broken down in vivo and subsequently resorbed. Both biodegradable and bioabsorbable materials are suitable for purposes of this application and thus for simplicity, unless otherwise directed, biodegradable materials and bioabsorbable materials are collectively referred to as "biodegradable" herein. Conversely, "non-biodegradable" is a biocompatible (i.e., not harmful to living tissue) material is not decomposed or broken down in vivo. In addition, the term "dissolution" as used in the description refers to the breakdown of both biodegradable and bioabsorbable materials.

The system 10 also includes a source 14 of perfusion fluid. Perfusion fluid may be any ionic aqueous based solution, such as saline. The source 14 may include a dispensing container 16 storing the perfusion fluid and a pump 18 configured to dispense and meter the perfusion fluid at a desired flow rate. The pump 18 may be any suitable pump such as a diaphragm pump, a gear pump, a piston pump, a peristaltic pump, a syringe pump. The dispensing container 16 may be configured to hold any suitable amount of fluid from about 50 milliliters (mL) to about 1 liter. The source 14 is coupled to a microcatheter 12 via a supply line 20. The microcatheter 12 may have an outer diameter from about 1 French size (Fr) to about 10 Fr and may be of any suitable length for reaching the anastomosis site "S" to outside the patient.

The perfusion fluid flows through the supply line 20 through the microcatheter 12. The pump 18 may be actively pumping the perfusion fluid at specific intervals or continuously. The pump 18 can be customized to specific flow rate and set to specific "risk intervals" given patient parameters. In embodiments, where patient has certain comorbidities (diabetes, smoking, obesity etc.), the monitoring interval can be longer and sampling more frequent.

The microcatheter 12 is also fluidly coupled to a collection container 26 (FIG. 3) via a return line 24. The collection container 26 may be a vial having a volume from about 20 µL to about 100 mL and is configured to receive the fluid from the microcatheter 12. The extracellular fluid is collected at the collection container 26. The extra cellular fluid is analyzed by a kinetic enzymatic analyzer 30, which may include a display 32.

With reference to FIG. 2, the system 10 is wearable by a patient following an anastomosis procedure and is completely portable device such that the patient can go home and resume normal activities sooner, which is a significant part of enhanced recovery after surgery protocol. The source 14 and the analyzer 30 are attachable to a belt 40, which allows for securing the system 10 to the patient while the microcatheter 12 is implanted at the anastomosis site "S".

The analyzer 30 displays the results of the analysis on the display 32, which may be a touchscreen. Displayed results may include concentrations of various bio markers indicative of an anastomotic leak, such as concentrations of glucose, pyruvate, lactate, lactate/pyruvate ratio (LPR), and glutamate. In addition, the analytic assay can be personalized to detect specific signaling molecules, besides metabolic parameters. The assay may be modified to track collagen and leak-specific markers as well. Thus, providing a comprehensive analysis of wound healing progress.

Pyruvate and lactate and their ratio are suitable biomarker since these parameters are representative of tissue oxygenation. In conditions of sufficient oxygen, the tissue takes up oxygen and excretes pyruvate. When oxygen is limited, tissue is hypoxic, then the same byproduct of pyruvate is further transformed into lactate. Thus, in a healthy tissue the expectation is a steady production of pyruvate, while in tumors or other septic tissue the levels of higher lactate are expected. Such ratio of L:P are predictive of how "healthy" the tissue is if the process of oxygenation is more typical of a healthy or diseased tissue.

The healthy blood levels for lactate that may be used by the analyzer 30 to determine whether the tissue is healthy may be from about 0.3 mmol/L to about 2.0 mmol/L and a concentration above 5 mmol/L is indicative of lactic acidosis, which that has negative systemic effect and requires clinical intervention. Healthy range for pyruvate may be from 0.030 mmol/L to about 0.110 mmol/L. Furthermore, the L:P ratio above approximately 25 may be indicative of negative clinical event. Thus, the analyzer 30 is configured to indicate that there is an anastomotic leak when at least one of the following concentrations of the collected extracellular fluid from at the anastomosis site "S" is above the following thresholds: pyruvate concentration is above 0.15 mmol/L, lactate concentration is above 5 mmol/L, and L:P ratio is above 25.

Lactate and pyruvate are descriptive of an anastomotic leak around day 5 or 6, the earliest detectable biomarkers that may also be measured include, TNF-α, interleukins IL-6 and IL-10. These biomarkers are detectable in intraperitoneal fluid that is collected in the drain after surgery and may also be analyzed in the extracellular fluid collected by the system 10. The detection ranges for TNF-α and IL-10 may be from about 7.8 pg/mL to about 500 pg/ml, and for IL-6 may be from about 4.7 pg/L to about 300 pg/ml, which may be measured using enzyme-linked immunosorbent assay (ELISA) reader. The analyzer may obtain a baseline reading for each of TNF-α, IL-6 and IL-10 on a first day after anastomosis is performed and obtain a second reading a day or two after the baseline reading, if concentrations are trending greater than the upper bound of the above-disclosed ranges, it would be indicative of possible leak.

The displayed results may also include safe ranges of the analyzed biomarkers. A clinician may then decide whether there is an anastomotic leak based on measured values being within ranges for the biomarkers that are indicative of the leak. In embodiments, the analyzer 30 may automatically determine status of the healing process of the anastomosis site "S", including the presence of an anastomotic leak, based on certain biomarkers being within prescribed ranges. The results of the determination may be displayed on the display 32.

Figure 3:
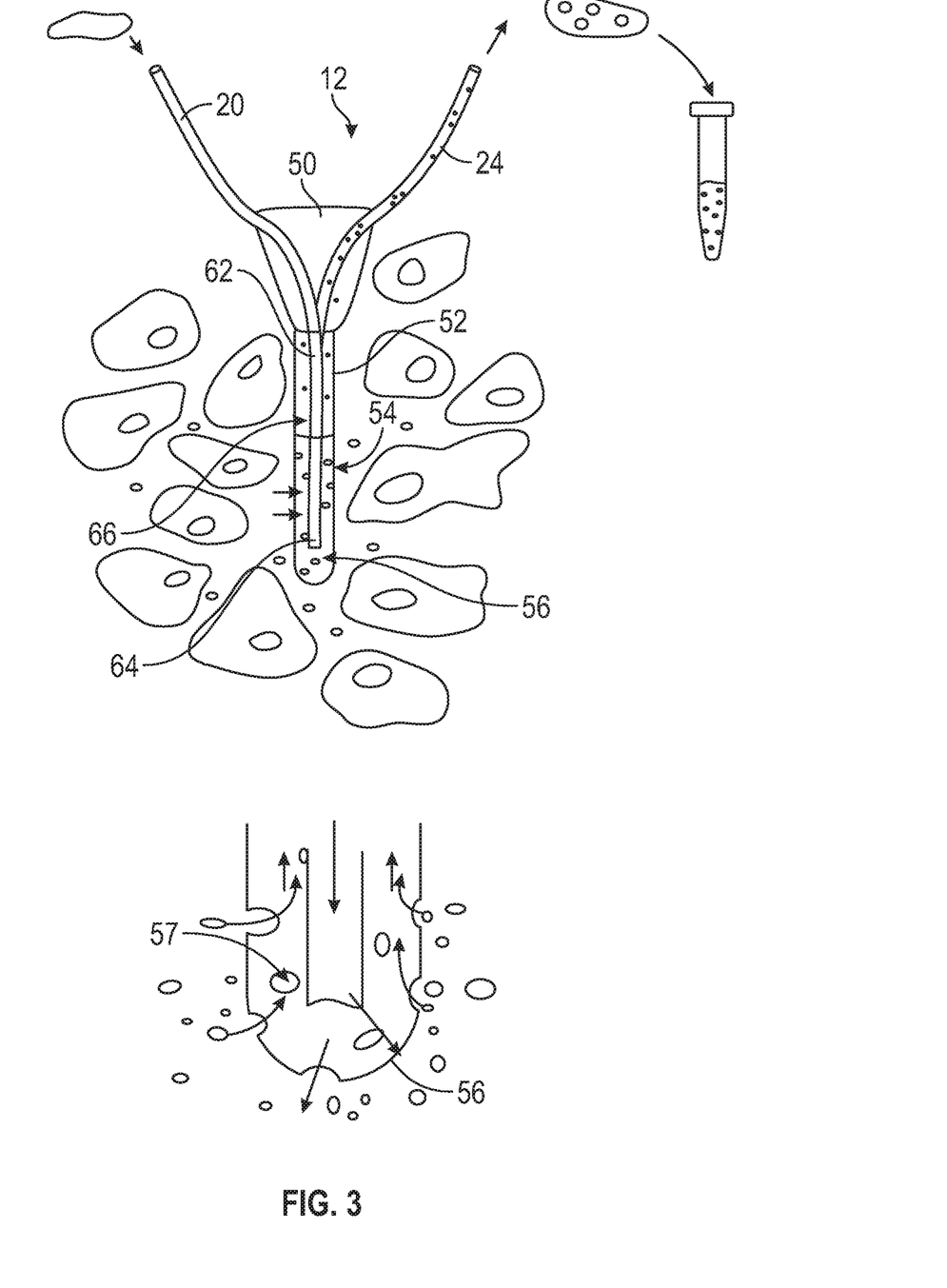
FIG. 3 is a schematic illustration of microcatheter implanted at the anastomosis site for use with the system of FIG. 1.

With reference to FIG. 3, the microcatheter 12 is shown in more detail. The microcatheter 12 includes a hub 50, which is coupled to and secures the supply line 20 and the return line 24. The microcatheter 12 also includes an outer tube 52, which is fluidly coupled to the return line 24. The outer tube 52 is also coupled to the hub 50. The outer tube 52 includes a distal portion 54 having a semipermeable membrane 56. The microcatheter 12 further includes an inner tube 62 that is fluidly coupled to the supply line 20. The inner tube 62 is disposed within a lumen 66 defined by the outer tube 52. During use, the perfusion fluid is supplied from the source 14 through the supply line 20 to the microcatheter 12. The perfusion fluid flows through a distal opening 64 of the inner tube 62 and fills the lumen 66.

The semipermeable membrane 56 may have a nanoporous structure allowing for diffusion of the perfusion fluid into the surrounding tissue at the anastomosis site "5" to generate a chemical gradient therein. Semipermeable membrane 56 may be a biological or synthetic, polymeric membrane that allow certain molecules or ions to pass through it by diffusion. In embodiments, the semipermeable membrane 56 may be formed from polyether sulfone or polysulfone. The exchange is possible due to the porous structure of the semipermeable membrane 56 having specifically sized pores 57 such that only specific analytes, namely, lactate, pyruvate, TNF-α, IL-6 and IL-10, can cross through the semipermeable membrane 56. In particular, the size of the pores prevents large molecules like peptides and proteins to get inside the microcatheter 12. This way the extracellular fluid collected does not need to be excessively filtered to be analyzed. Lactate, pyruvate and cytokines, and other biomarkers of interest are smaller molecules and can cross over and be collected.

Chemical gradient generated by the presence of the perfusion fluid at the anastomosis site "S" drives molecular diffusion across the semipermeable membrane 56. The perfusion fluid is exchanged at the anastomosis site "S" with extracellular fluid. The chemical gradient refers to concentration difference that exists across a biological membrane, where the concentration of ions in the perfusion fluid is higher on one side of the membrane 56 compared to the other side and similarly concentration of analytes of interest, e.g., biomarkers, of the extracellular fluid. After the microcatheter 12 is implanted at the anastomosis site "S" and the perfusion fluid is supplied thereto, the perfusion fluid inside the outer tube 52 has a lower concentration of biomarker molecules than the extracellular fluid outside of the outer tube 52. The molecules strive to reach an equilibrium, namely, to achieve the same concentration inside and outside the outer tube 52 via diffusion. Thus, extracellular fluid permeates into microcatheter 12, and is then be pumped out and collected for sampling.

The extracellular fluid being collected from the site is significantly more "filtered" than blood serum that is traditionally used for detection, due to semi-permeability of the membrane 56. Blood serum used for detection produces inferior detection results, because pyruvate levels are relatively low, but the concentrations of other blood agents are high, that drives the need for expensive and highly sensitive sensors, which prevents from mass-use of such sensors.

Figure 4:
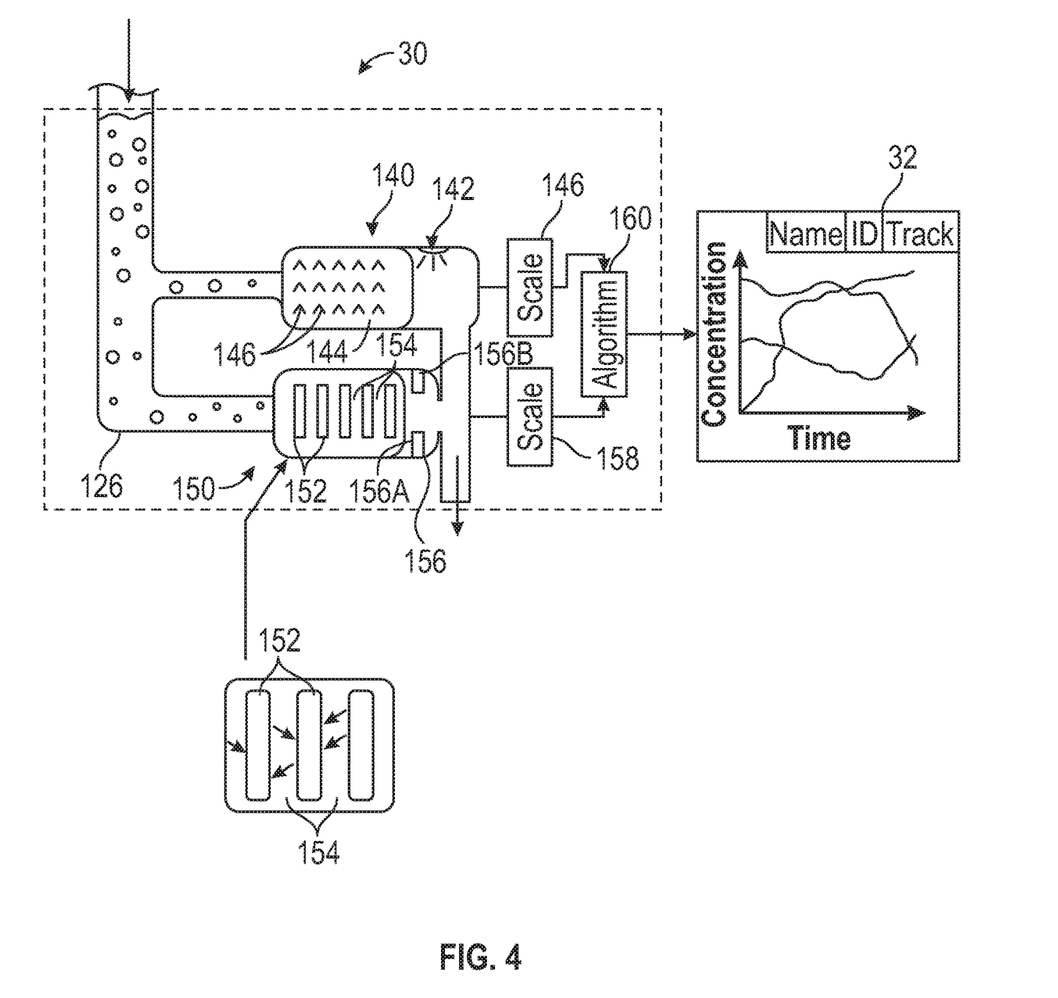
FIG. 4 is a schematic diagram of an analyzer for use with the system of FIG. 1.

With reference to FIG. 4, the components and functionality of the analyzer 30 is described. The analyzer 30 is based on enzymatic detection, which is considered superior to other conventional methods due to its accuracy and precision. The fundamentals of this method imply having a specific reagent inside the sensor that will bind to the analytes (e.g., lactate, pyruvate, etc.) and produce a reaction, that would usually induce a color change or change in shape of the analyte (e.g., cross-linking). The intensity of color change or shape change is then correlated to the concentration of analyte.

The extracellular fluid from the microcatheter 12 is pumped into the collection chamber 126 and divided between a lactate sensor 140 and a pyruvate sensor 150. The lactate sensor 140 is an enzyme-fluorometry sensor, in which lactate is oxidized with lactate dehydrogenase, which acts as a reactant and reacts with lactate to form nicotinamide adenine dinucleotide and hydrogen (NADH). NADH occurs naturally in the body and plays a role in the chemical process that generates energy. NADH is also naturally fluorescent and can be detected by an LED light 142 at wavelength of about 340 nm, which is a specific wavelength to detect NADH levels and consequently lactate levels. The lactate sensor 140 is coated with a carbon nanotubules layer 144 and with microelectrodes 146, which may be formed from any suitable conductor, such as gold or platinum. The layer 144 and the microelectrodes 146 enhance sensitivity and extend the operating life of the lactate sensor 140. Sensor 142 is linked to a scale 148, which is coupled to a processor 160.

The pyruvate sensor 150 includes a plurality of electrodes 152 and a plurality of active surfaces 154 having antigens disposed thereon. The pyruvate from extra cellular fluid reacts with antigens on active surfaces 154 and its electrons migrate into the electrodes 152. The amount of these electrodes 152 is quantified by an optical sensor 156 and the value is fed to a scale 158, which is also coupled to the processor 160. The analyzer 30 also includes additional sensors for determining concentration of TNF-α, IL-6 and IL-10.

The processor 160 may be any suitable processor operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor 160 may be any control circuit adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

The processor 160 is configured to execute an application for analyzing the analyte concentrations. In particular, the processor 160 is configured to receive two scaled outputs from the scales 148 and 158 of the lactate sensor 140 and the pyruvate sensor 150, respectively. The processor 160 calculates ratio of lactate to pyruvate (L:P) and compiles the absolute values for the samples and the trending pattern over a period of time of lactate, pyruvate and of L:P ratio. This data is then displayed on a graphic user interface on the display 132 and can be communicated to the clinicians.

The analyzer 30 is also configured to wirelessly transmit data to other computing devices, e.g., hospital network, remote outpatient facility, allowing for remote monitoring of the anastomotic leaks. This allows for reducing the number of hospital visits and narrowing down the pool of patients with complications that require medical help. The analyzer 30 may be connected to other devices using any suitable communication network based on wired or wireless communication protocols. The term "network," whether plural or singular, as used herein, denotes a data network, including, but not limited to, the Internet, Intranet, a wide area network, or a local area networks, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 802.15.4-2003 standard for wireless personal area networks (WPANs)).

In further embodiments, one the analyzer 30 detects the anastomotic leak, the source 114 may be used to treat the anastomotic leak. In particular, the microcatheter 112 is already disposed at the anastomosis site "S", the microcatheter 112 provides a direct passageway to the anastomosis site "S" for delivery of fluids. In embodiments, once a clinician is notified of the leak, the clinician may reconfigure the source 114 to dispense medication, e.g., antibiotics, clotting agents, etc. to treat the anastomotic leak. The dispensing container 116 containing the perfusion fluid may be replaced with another dispensing container 116 containing medication, thereby using the same configuration to treat the anastomotic leak.

The systems 10 and 100 for detecting an anastomotic leak according to the present disclosure may also be used following any abdominal surgery to predict early ischemia, which renders the gastrointestinal tract a source of bacteria, endotoxins, free radicals, and inflammatory agents with detrimental effects to health. Lactate and pyruvate and their ratio are biomarkers of particular interest since they are predictive signaling parameters of compromised tissue healing. The patient will be able to be more active and resume his daily tasks in his familiar environment, which will enhance the recovery. The hospital will benefit by sending the patient home sooner, and in case of complication—early resolution will be through diagnostics and therapy, instead of surgery, thus cutting the main contributing costs.

Figure 5:
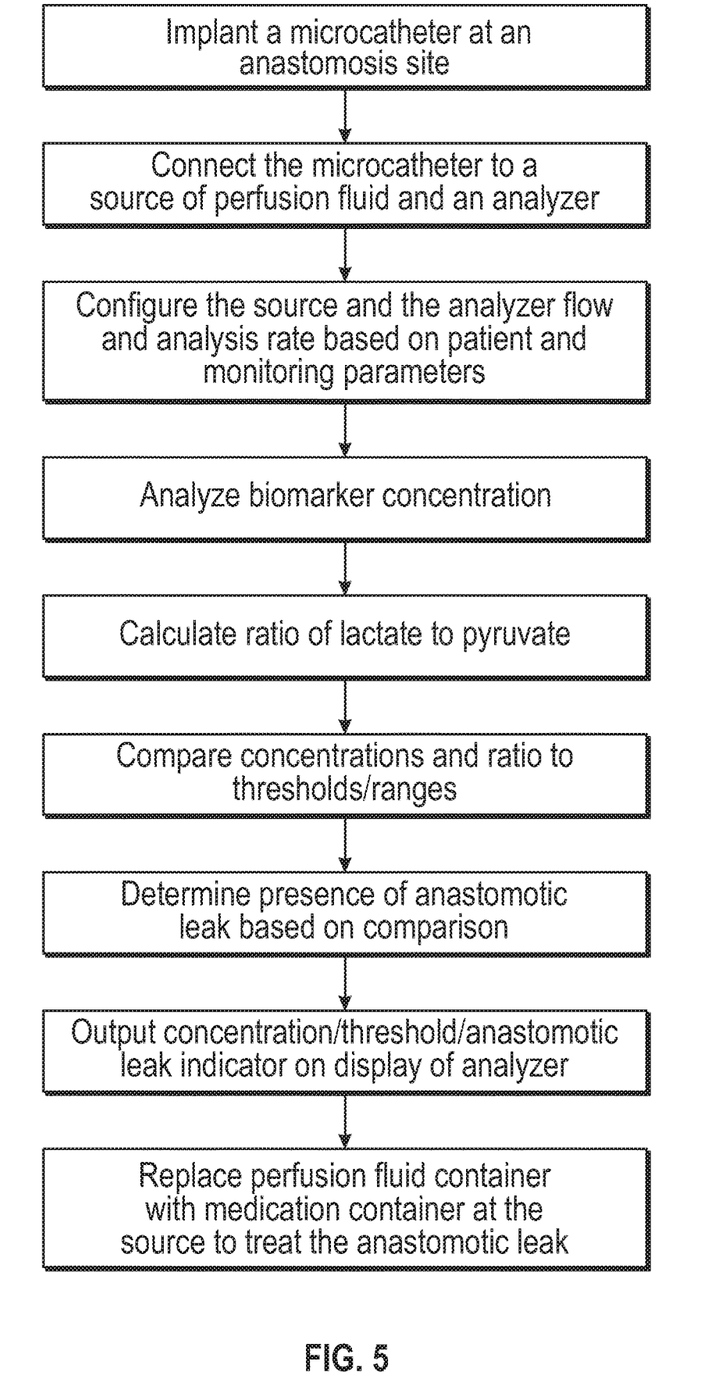
FIG. 5 is a flow chart of a method for detecting and treating an anastomotic leak according to the present disclosure.

With reference to FIG. 5, a method for detecting and treating an anastomotic leak using the system 10 according to the present disclosure includes initially implanting the microcatheter 12 at the anastomosis site "S". The microcatheter 12 is then coupled to the source 14 and the analyzer 30. The source 14 and the analyzer 30 are configured to operate at a desired flow rate that is configurable by a clinician. The flow rate may be based on patient and other monitoring parameters to continuously or periodically pump the perfusion fluid into the microcatheter 12, which then collects the extracellular fluid, that is then analyzed by the analyzer 30. In particular, the analyzer 30 measures concentrations of lactate and pyruvate and determines a ratio of lactate to pyruvate. Any one of these parameters, as well concentrations of other biomarkers, such as TNF-α, IL-6 and IL-10, may also determined. The concentrations along with thresholds and alarms may be displayed on the display 32 and analyzed by a clinician who then determines the status of the healing process of the anastomosis site "S", including the presence of an anastomotic leak. The analyzer 30 may also determine concentrations and the ratio of L:P are then compare the concentrations to predetermined thresholds to determine the status of the healing process of the anastomosis site "S", including the presence of an anastomotic leak. If the leak is present, the analyzer 30 outputs a message indicating as such. The source 14 may then be reconfigured to output medication to treat the anastomotic leak.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

What is claimed is:

1. A system for detecting and treating an anastomotic leak, the system comprising:
   a microcatheter implanted at an anastomosis site;
   a wearable source of a perfusion fluid coupled to the microcatheter and configured to dispense the perfusion fluid to the microcatheter;
   a wearable analyzer coupled to the microcatheter configured to receive an extracellular fluid from the microcatheter and to analyze the extracellular fluid to determine status of the anastomosis site, the analyzer including:
      a lactate sensor configured to measure a concentration of lactate;
      a pyruvate sensor configured to measure a concentration of pyruvate;
      a processor configured to:
         calculate a ratio of the concentration of lactate to the concentration of pyruvate; and
         indicate the status of the anastomosis site based on the ratio of the concentration of lactate to the concentration of pyruvate.

2. The system according to claim 1, wherein the microcatheter includes:
   an outer tube having a distal portion formed from a semipermeable membrane and defining a lumen within the outer tube; and
   an inner tube disposed within lumen.

3. The system according to claim 2, wherein the outer tube is fluidly coupled to a return line and the inner tube is fluidly coupled to a supply line.

4. The system according to claim 3, wherein the return line is coupled to the analyzer and the supply line is coupled to the source of the perfusion fluid.

5. The system according to claim 1, wherein the source of the perfusion fluid includes:
   a dispensing container including the perfusion fluid; and
   a pump fluidly coupled to the dispensing container and configured to meter the perfusion fluid at a configurable flow rate.

6. The system according to claim 1, wherein the analyzer further includes:
   a display coupled to the processor, the display configured to display a value selected from the group consisting of the concentration of lactate, the concentration of pyruvate, and the ratio of the concentration of lactate to the concentration of pyruvate.

7. The system according to claim 6, wherein the display is configured to display a plot over time of the value.

8. A system for detecting and treating an anastomotic leak, the system comprising:
   a microcatheter implanted at an anastomosis site;
   a source of a perfusion fluid coupled to the microcatheter and configured to dispense the perfusion fluid to the microcatheter; and
   an analyzer coupled to the microcatheter configured to receive an extracellular fluid from the microcatheter and to analyze the extracellular fluid to determine a presence of an anastomotic leak, the analyzer including:
      a lactate sensor configured to measure a concentration of lactate;
      a pyruvate sensor configured to measure a concentration of pyruvate;
      a processor configured to:
         calculate a ratio of the concentration of lactate to the concentration of pyruvate;
         and
         indicate the presence of the anastomotic leak based on the ratio of the concentration of lactate to the concentration of pyruvate.

9. The system according to claim 8, wherein the microcatheter includes:
   an outer tube having a distal portion formed from a semipermeable membrane and defining a lumen within the outer tube, the outer tube is fluidly coupled to a return line, which is coupled to the analyzer; and
   an inner tube disposed within lumen, the inner tube is fluidly coupled to a supply line, which is coupled to the source of the perfusion fluid.

10. The system according to claim 8, wherein the source of the perfusion fluid includes:
    a dispensing container including the perfusion fluid; and
    a pump fluidly coupled to the dispensing container and configured to meter the perfusion fluid at a configurable flow rate.

11. The system according to claim 8, wherein the analyzer further includes:
    a display coupled to the processor, the display configured to display a value selected from the group consisting of the concentration of lactate, the concentration of pyruvate, and the ratio of the concentration of lactate to the concentration of pyruvate.

* * * * *